US006669662B1

(12) United States Patent
Webler

(10) Patent No.: US 6,669,662 B1
(45) Date of Patent: Dec. 30, 2003

(54) PERFUSION CATHETER

(75) Inventor: William E. Webler, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/752,871

(22) Filed: Dec. 27, 2000

(51) Int. Cl.⁷ .............................. A61M 1/00; A61M 5/00
(52) U.S. Cl. ........................ 604/35; 604/507; 604/511; 604/151; 604/165.04
(58) Field of Search ................... 604/35, 151, 505, 604/507, 508, 511, 93.01, 164.01, 164.02, 164.03, 164.04, 164.05, 164.07, 164.08, 164.09, 166.01, 167.01, 167.03, 167.05, 165.01, 165.02, 165.04, 246, 248, 249, 256

(56) References Cited

U.S. PATENT DOCUMENTS

| | | | |
|---|---|---|---|
| 4,661,094 A | | 4/1987 | Simpson |
| 4,771,777 A | | 9/1988 | Horzewski et al. |
| 4,790,315 A | | 12/1988 | Mueller, Jr. et al. |
| 4,887,605 A | | 12/1989 | Angelsen et al. |
| 5,092,844 A | * | 3/1992 | Schwartz et al. ............. 600/16 |
| 5,115,814 A | | 5/1992 | Griffith et al. |
| 5,137,513 A | | 8/1992 | McInnes et al. |
| 5,163,910 A | * | 11/1992 | Schwartz et al. ............. 600/16 |
| 5,193,546 A | | 3/1993 | Shaknovich |
| 5,195,971 A | | 3/1993 | Sirhan |
| 5,263,963 A | | 11/1993 | Garrison et al. |
| 5,318,535 A | | 6/1994 | Miraki |
| 5,356,388 A | | 10/1994 | Sepetka et al. |
| 5,370,617 A | | 12/1994 | Sahota |
| 5,409,455 A | | 4/1995 | Belden |
| 5,411,016 A | | 5/1995 | Kume et al. |
| 5,497,782 A | * | 3/1996 | Fugoso ....................... 600/585 |
| 5,501,667 A | | 3/1996 | Verduin, Jr. |
| 5,507,795 A | * | 4/1996 | Chiang et al. ............... 606/167 |
| 5,516,336 A | | 5/1996 | McInnes et al. |
| 5,527,292 A | | 6/1996 | Adams et al. |
| 5,571,089 A | | 11/1996 | Crocker |
| 5,573,508 A | | 11/1996 | Thornton |
| 5,573,509 A | | 11/1996 | Thornton |
| 5,591,129 A | | 1/1997 | Shoup et al. |
| 5,599,307 A | | 2/1997 | Bacher et al. |
| 5,632,754 A | | 5/1997 | Farley et al. |
| 5,667,521 A | * | 9/1997 | Keown ....................... 606/194 |
| 5,716,410 A | | 2/1998 | Wang et al. |
| 5,746,709 A | * | 5/1998 | Rom et al. ....................... 604/8 |
| 5,749,852 A | | 5/1998 | Schwab et al. |
| 5,772,632 A | | 6/1998 | Forman |
| 5,782,740 A | * | 7/1998 | Schneiderman ................ 600/1 |
| 5,807,328 A | * | 9/1998 | Briscoe ..................... 604/102.02 |
| 5,830,181 A | * | 11/1998 | Thornton ................. 604/102.01 |
| 5,833,688 A | | 11/1998 | Sieben et al. |
| 5,855,546 A | | 1/1999 | Hastings et al. |
| 5,891,090 A | | 4/1999 | Thornton |
| 5,989,218 A | * | 11/1999 | Wasicek ................. 604/164.13 |
| 6,027,460 A | * | 2/2000 | Shturman ..................... 600/129 |
| 6,102,903 A | * | 8/2000 | Tremulis ..................... 604/249 |
| 6,110,097 A | * | 8/2000 | Hastings et al. ................. 600/3 |
| 6,217,595 B1 | * | 4/2001 | Shturman et al. ........... 242/430 |
| 2002/0032457 A1 | * | 3/2002 | Sirhan et al. ................ 606/195 |

FOREIGN PATENT DOCUMENTS

EP 0761252 * 3/1997 .......... A61M/29/02

* cited by examiner

Primary Examiner—Henry C. Yuen
Assistant Examiner—Hai Huynh
(74) Attorney, Agent, or Firm—Blakely, Sokoloff, Taylor & Zafman, LLP

(57) ABSTRACT

A perfusion catheter with a shaft having a lumen and a plurality of ports through the shaft. A rotatable core with a core groove is disposed within the lumen. The plurality of ports can be exposed by retraction of the core. The core can be rotated within the shaft.

43 Claims, 4 Drawing Sheets

PERFUSION CATHETER

BACKGROUND OF THE INVENTION

This invention relates generally to catheters which are utilized within narrowed vasculature such as at the site of a stenosis. More particularly, the present invention deals with catheters allowing blood perfusion within such narrowed vasculature.

BACKGROUND OF THE PRIOR ART

Atherosclerosis, the progressive narrowing and hardening of blood vessels over time, may often result in a disabling blockage or narrowed vessel walls. Traditionally, when the blockage involved coronary vasculature, treatment was by way of a coronary bypass operation. The bypass involves placing the patient under general anesthesia, opening the patient's chest cavity and surgically grafting a vein or artery from another part of the patient's body onto the patient's coronary artery. The bypass operation is very traumatic, difficult and expensive. Recovery time is long and painful with a less than certain outcome. Additionally, relief is often only temporary.

Due to the drawbacks of coronary bypass operations, minimally invasive treatment methods, allowing the blockage to be treated selectively and locally, are becoming more common. This type of surgery will most likely employ a catheter to deliver a host of devices to the site of the blockage. These devices may be balloons, stents, drug or radiation delivery devices or a host of other devices for selectively treating the blocked artery at the site of the blockage. The patient will often experience immediate relief along with a brief, more comfortable and less expensive recover. However, a catheter is generally prone to create an ischemic condition when passing through a narrowed vessel.

To be effective, a cardiac catheter must be placed and utilized with great precision. The catheterization team needs to know measurements including location, size, shape and consistency of the blockage (atheroma) as well as the surrounding arterial structures. Therefore visualization by the use of ultrasound allow for visual monitoring of the treatment being performed. Intravascular ultrasound (IVUS) imaging or other visualization techniques may be performed with an imaging device delivered to the site of interest. Imaging allows the measurements above to be made, thus, making treatment more effective.

The IVUS catheter has a tubular shaft surrounding an inner core. The core is rotatable, and usually longitudinally translatable, within the shaft. The shaft prevents the rotating core from damaging vasculature when inserted thereinto. Conventional practice is to first locate the stenosis site by angiography (i.e. injection of contrast material into a blood vessel for external imaging purposes). The stenosis is then traversed with a guidewire. The guidewire may be inserted into the patient's femoral artery through a small puncture wound in the patient's upper thigh. The IVUS catheter is then inserted over the guidewire. The IVUS catheter is positioned to allow intravascular ultrasound measurement and imaging of the artery, a distal and proximal reference segment thereof and the entire length of the stenotic region. The core is preferably translated longitudinally as far distal as practicable during IVUS catheter insertion in order to support the shaft, especially at a thin imaging zone at the distal portion of the shaft.

The distal end of the core includes an ultrasonic transducer. The transducer emits short pulses of ultrasound toward the wall of the artery. As the ultrasound enters the blockage and passes through surrounding tissue, the structures within the blockage, and various layers thereof, echoes are returned. An image is built by directing pulses at different parts of the artery. The pulses are directed by rotating the core and thus the transducer. With each rotation, a cross-section is assembled into a fairly detailed two-dimensional picture of the artery as viewed from the inside thereof. The shaft, which is relatively transparent to the ultrasound, prevents the shaft from scraping or battering the artery wall.

Once inserted to a position adjacent the stenosis, the preferred practice is to start imaging with the core advanced to a distal most position within the shaft. Images are recorded as the core is moved (i.e. longitudinally translated) proximally, within the stationary shaft, until the entire artery has been imaged. This practice is known as a pullback. This provides a complete record of the stenosis site and the vasculature used to access the stenosis. The IVUS catheter is then removed and the recorded images examined and measured, as directed by the physician The shaft is often large enough to completely block the artery (i.e. ischemia) when placed across the stenosis. As a result, the patient will often experience increasing pain and distress when the IVUS shaft is introduced into the target area. In response to the ischemia the physician will often withdraw the shaft far enough proximal to the blockage to restore blood flow. Before imaging can continue, time is lost as the heart muscle recovers sufficiently to withstand another possible ischemic episode.

The inefficiency which results from the shaft induced ischemia is better understood when considering that an effective pullback may need to last as long as 100 to 200 seconds. This does not count the time necessary for catheter placement and any preliminary imaging the physician may wish to perform. While the amount of effective time required during the procedure may be somewhat limited as noted above, the actual time necessary to accomplish the procedure is greatly affected by the number of ischemic episodes which result. Furthermore, the effective time is long enough such that once an ischemic condition is caused at the target are, it is likely to reappear several times before the procedure is completed. Not only does this affect the procedure but it affects the patient as well. That is, withdrawing and reinserting the shaft through the stenosis can injure the artery and may dislodge material from the stenosis. An injured artery or disrupted stenosis is more likely to form blood clots or another stenosis. Similar occlusion problems can result with other catheter devices as well. Therefore, what is desired is a perfusion catheter having features to enhance perfusion during an intravascular procedure.

SUMMARY OF THE INVENTION

In an embodiment of the invention a perfusion catheter is provided with a shaft having a lumen and a plurality of ports through the shaft. A rotatable core having a core groove is disposed within the lumen.

In a method of the invention circulation in a vessel is allowed for while a catheter shaft housing a retractable core and having a plurality of ports is placed across the vessel. The retractable core is retracted to expose a portion of the plurality of ports and allow a flow of blood into a shaft lumen of the catheter shaft.

In an alternate method of the invention circulation in a vessel is maintained during a catheterization procedure. A catheter shaft having a plurality of ports is guided to the vessel. A core having a core groove is rotated within a lumen of the shaft.

BRIEF DESCRIPTION OF THE DRAWINGS

The invention is further described by way of example with reference to the accompanying drawings, wherein.

DETAILED DESCRIPTION OF THE INVENTION

Figure 1:
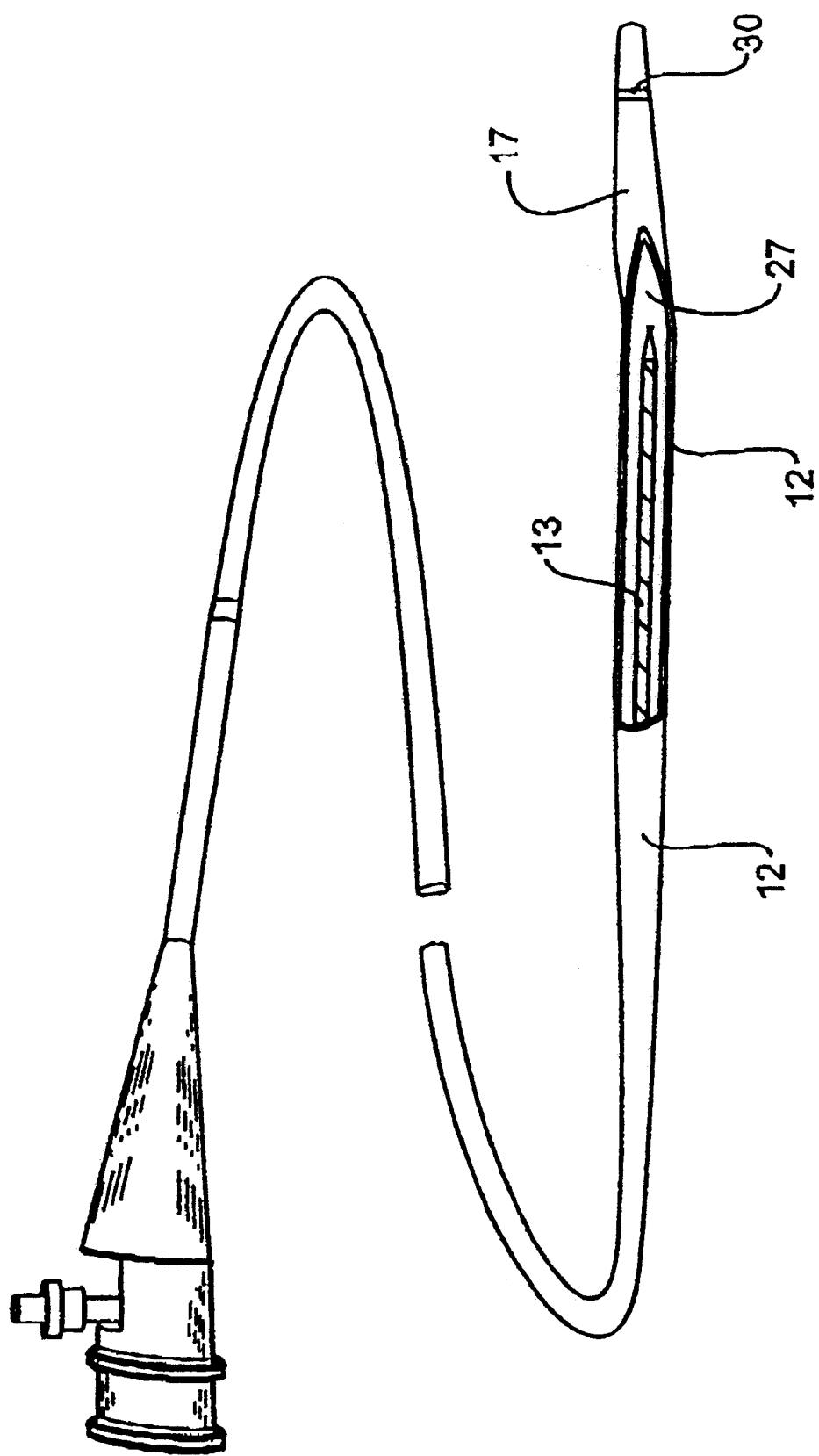
FIG. 1 is a partially sectioned pictorial view of an embodiment of a perfusion catheter of the present invention.
Figure 2:
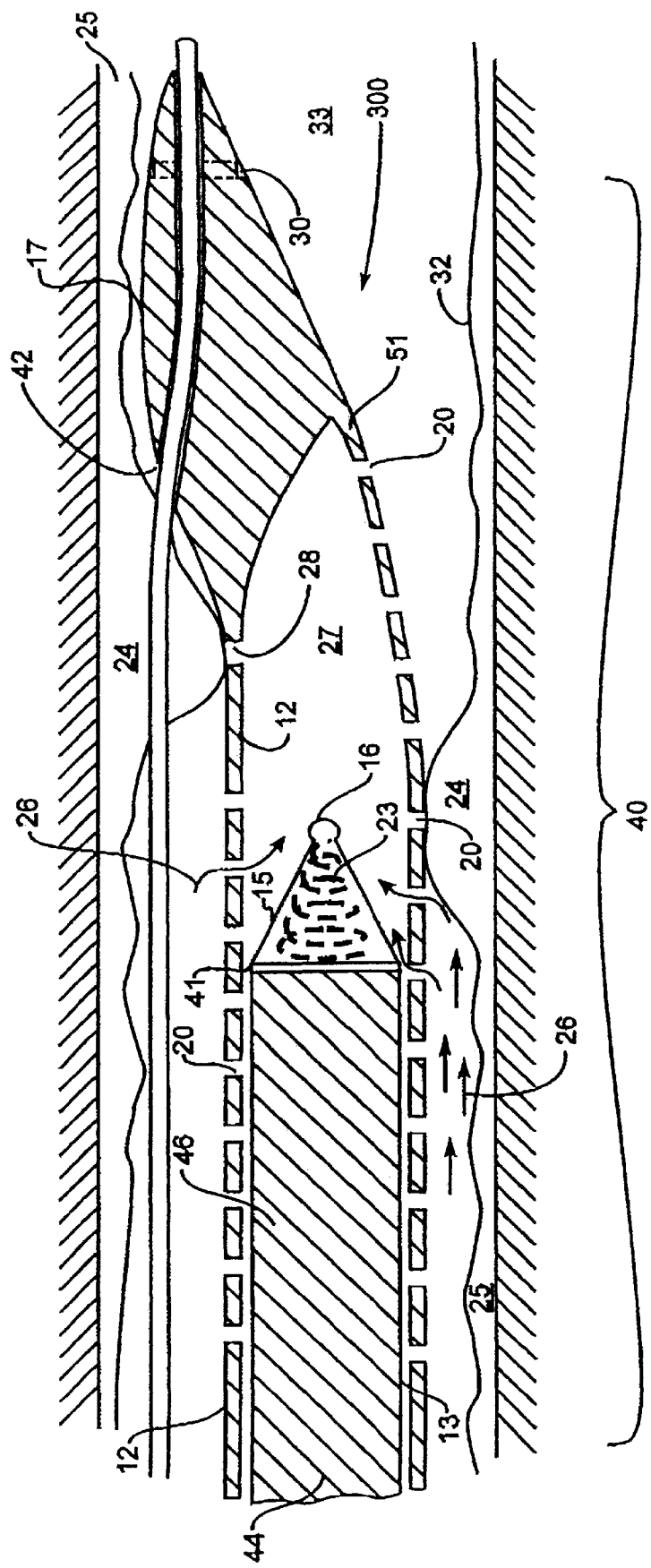
FIG. 2 is a cross-sectional view of the embodiment of FIG. 1 placed within a stenosed artery.
Figure 3:
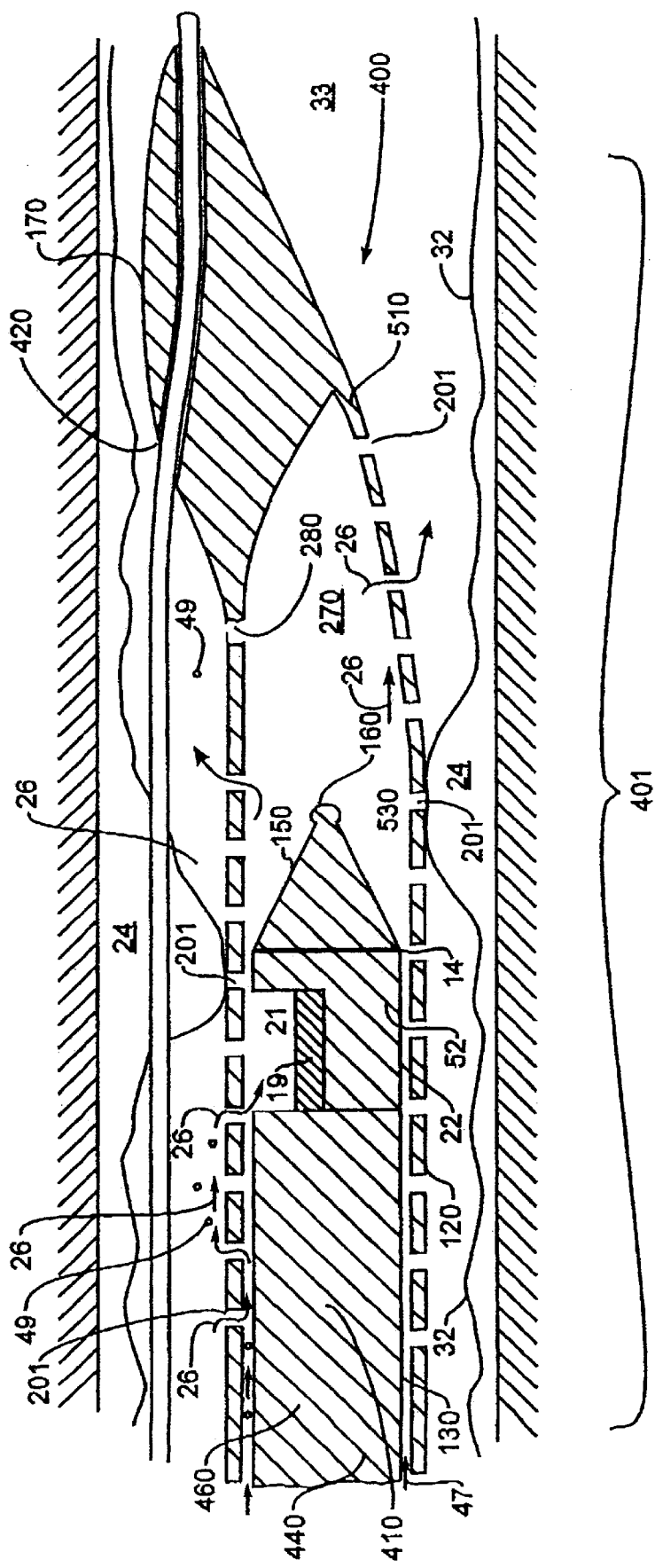
FIG. 3 is a cross-sectional view of an alternate embodiment of an imaging perfusion catheter within a stenosed artery.

Referring to FIGS. 1–4, embodiments of perfusion catheters 300, 400, 500 of the present invention are shown. Specifically, FIG. 1 illustrates an embodiment of a perfusion catheter alone, while FIGS. 2 and 3 illustrate embodiments of perfusion catheters 300, 400 within a stenosed artery 25. The perfusion catheter 400 of FIG. 3 is equipped with an imaging device 22 which has been placed within a stenosed artery 25 and retracted proximally.

Referring to FIG. 2, the catheter 300 embodiment shown includes a longitudinal shaft 12 with shaft lumen 27 therethrough. A rotatable core 13 is disposed therein. The core 13 is rotatable within the shaft 12 and may be moved longitudinally within the shaft 12. A monorail tip 17 is provided with a guidewire lumen 42 there through. A distal tip marker 30 is incorporated into the monorail tip 17.

In one embodiment the guidewire lumen 42 is approximately 0.016 inches in diameter. In another embodiment the shaft 12 will have an inner diameter of approximately 0.033 inches and an outer diameter of approximately 0.043 inches. The core 13 is approximately 0.030 inches in diameter.

A plurality of ports 20 allows fluid communication between the arterial passage 33 and the shaft lumen 27. In various embodiments, the plurality of ports 20 may have various shapes. In one embodiment the plurality of ports 20 is as small as is practicable for the effective perfusion of blood as large as necessary to protect the coronary artery 25 from the rotating core 13. That is, embodiments of the invention do not include ports 20 large enough to allow portions of the coronary artery 25 to penetrate the shaft 12 via the ports 20.

The size, number, disbursement, and shape of the plurality of ports 20 is varied in alternate embodiments depending upon the flow rate and variance to be achieved. In one embodiment the shaft 12 is manufactured with a permeable screen or mesh in order to provide the plurality of ports 20 where desired. However, care should be taken to preserve the structural integrity of the shaft 12 and prevent its entanglement with the coronary artery 25 (or an imaging device 22 as seen in FIG. 3) and floppy tip 15, discussed further herein. A larger flush port 28 may also be provided near the distal end of the lumen 27.

Embodiments of the catheter 300 are designed to allow the core 13 to be advanced to within a short distance of the distal shaft 51 without completely blocking the plurality of ports 20. In one embodiment, the length of the core 13 is less than the length of the shaft 12 and equipped with a stopping mechanism at the proximal end of the core (not shown) in order to prevent slippage of the entire core 13 into the lumen.

In one embodiment, the distal end 41 of the core 13 also includes a floppy tip 15. The floppy tip 15 is constructed with a floppy tip coil 23. The floppy tip 15 terminates in a ball 16. Up to about 4 mm may separate the ball 16 from the distal shaft 51 when the core 13 is at its distal-most position. The shorter length of the core 13 in combination with the shape of the floppy tip 15 is to prevent the floppy tip 15 from ever making flush contact with the distal shaft 51 and thereby prevents complete blockage of the plurality of ports 20 (or the flush port 28 as provided in one embodiment).

Referring to FIG. 3 an alternate embodiment is shown where a core 130 is slightly withdrawn from the distal end of a stationary shaft 120. As the core 130 is retracted the fluid communication between the arterial passage 33 and the shaft lumen 270 increases due to the increased exposure of a plurality of ports 201. However, as noted above, distal movement of a core 130 would not eliminate all communication between the arterial passage 33 and the shaft lumen 270. Once the core 130 is withdrawn exposing the plurality of ports 201 a maximum communication between the arterial passage 33 and the shaft lumen 270 is present.

As shown in FIG. 3, the shaft 120 is in direct and complete circumferential communication with the stenosed arterial segment 24. Nevertheless, the plurality of ports 201 has prevented occlusion. The plurality of ports 201 have allowed a flow of blood 26 into the shaft lumen 270 proximal to the stenosed arterial segment 24. The flow of blood 26 continues within the shaft lumen 270 until it exits the plurality of ports 201 distal to the stenosed arterial segment 24. Even with the core 130 positioned at the relatively distal location shown, a significant flow of blood 26 can bypass the stenosed arterial segment 24 by way of the plurality of ports 201. As long as enough blood flows through the plurality of ports 201 to prevent ischemia, imaging or other procedures can proceed while the shaft 120 remains stationary in the area of interest. Consequently, the procedure is less traumatic to the patient and more efficiently performed.

In an embodiment of the invention the core 130 is retracted and the available volume of the shaft lumen 27 increases the flow of blood 26 bypassing the stenosed arterial segment 24. Additionally, in the embodiment shown, the core 130 is not in direct and complete circumferential contact with the shaft lumen 270. Therefore, some flow of blood 26 is capable of entering the shaft lumen 270 across portions of the shaft 120 which are not necessarily distal to the position of the core 130. This capability is enhanced by a core groove 440 discussed further here.

While there is limited space between the core 130 and the shaft 120 vertically (as depicted), the core 130 has a core groove 440 cut into its surface which acts to draw in, propel, and eventually expel fluid (plasma or otherwise) and air with respect to the shaft lumen 270. The core groove 440 is spiral in nature. With reference to the core 130 being at a distal most position within the shaft 120, the core groove 440 would originate on the core 130 at a point proximal to an imaging zone 401 of the shaft 120.

In one embodiment the core groove 440 is the result of the core 130 being comprised of a spring 460. The spring 460 is an outer spring wound around an inner spring (not shown) to form a duplex spring core. For integrity, the inner spring (not shown) is wound oppositely from the outer spring in one embodiment. Even in a compressed state a coil of the spring 460 will have a space or a channel between adjacent turns of the coil. This space provides the core groove 440.

Consider the spring 460 to have been wound from its proximal end distally. When the core 130 is rotated in the direction of the coil of the spring 460 the core groove 440 will visually appear to travel proximally. However, the core 130 rotates in an opposite direction the core groove 440 will appear to travel distally. When the core 130 rotates in this opposite direction it has the capacity to carry fluid distally by way of the core groove 440. For optimum rotational properties in an embodiment of the invention, this is the direction of rotation for a duplex spring core.

The plurality of ports 201 is shown extending proximally from the monorail tip 170, throughout an imaging zone 401. However, in an alternate embodiment the plurality of ports 20 is not entirely throughout the imaging zone 401. In the embodiment of FIG. 3, the core 130 has a distal end 410 with an imaging device 22 secured thereto. The imaging device 22 includes a housing 14 made of high strength steel or other suitable material. The housing 14 includes an opening 21 within which a transducer 19 has been disposed. The transducer 19 will emit ultrasonic vibrations into surrounding fluid (plasma or otherwise) and receive echoes of the emission.

The imaging device 22 is operable as the core 130 is rotated within the shaft lumen 270. This rotation of the imaging device 22, which carries the transducer 19, creates a single image which is a complete 360° depiction of the stenosed arterial segment 24. This image is obtainable while the shaft 120 remains stationary within the coronary artery 25. As imaging proceeds, the imaging device 22 is retracted proximally. The inner surface 32 of the coronary artery 25 will be protected from the rotating core by the shaft 120.

The more distal portion of the IVUS catheter 400 includes an imaging zone 401. In the embodiment of FIG. 3 the imaging zone 401 is large enough so as to occupy the length of a coronary artery 25. With respect to FIG. 3, all portions of the catheter 400 shown are within the imaging zone 401. That is, the transducer 19 is capable of emitting ultrasound and receiving echoes through the shaft 12 throughout the length of the portions of catheter 400 shown. In alternate embodiments, portions of the catheter 400 proximal to the imaging zone 401 do not allow the transducer to emit ultrasound and receive echoes beyond the shaft 120.

The transducer 19 requires fluid contact in order to properly transmit ultrasound and detect echoes. As a result, a flush 47, which is provided to the shaft lumen 270 at a proximal location, is forced distally across the core 13, eventually reaching the transducer 19. The core groove 440 helps carry the flush 47 to the transducer 19. That is, the transducer 19 is rotated by the core 13 in a direction which cooperates to simultaneously force the flush 47 distally within the shaft lumen 27. The housing 14 itself may have a housing groove 52 contiguous with the core groove 440 to help propel fluid past the entire imaging device 22 and out the plurality of ports 200 at the distal shaft 51. In one embodiment the housing groove 52 is a spiral cut into the surface of the housing 14. In another embodiment a floppy tip groove 53 is spirally cut into the surface of the floppy tip 150 and contiguous with the housing groove 52.

In some cases the flush 47 is accompanied by small air bubbles 49 that could obstruct the transducer 19 or a desired viewing location. Preventing such an occurrence, the present invention provides a plurality of ports 201 through which air bubbles 49 will exit the shaft lumen 270 and be readily absorbed by the blood. In fact, the air bubbles 49 begin to disintegrate while still within the shaft lumen 270 due to the agitation provided by a rotating core 130 in combination with the presence of a significant blood flow 26 within the shaft lumen 270, which would have the unique ability to bind and absorb the air bubbles 49.

As stated earlier, there is limited space between the core 130 and the shaft 120 vertically. However, the rotation of the core groove 440 acts to propel the flush 47 in a distal direction. This propulsion within the shaft lumen 270 creates a Bernoulli effect. That is, the pressure within the shaft lumen 270 is less than the pressure outside the shaft lumen 270 in the arterial passage 33. As a result, the lower pressure draws a blood flow 26 into the shaft lumen 270 through the plurality of ports 201 in spite of the limited space between the core 130 and the shaft 120. The drawing in of a blood flow 26 at this point helps ensure that some amount of circulation will proceed past the stenosed arterial segment 24 where it can reenter the blood stream through the plurality of ports 201 at the distal shaft 51.

The pumping action available from the rotation of the core groove 440 is further enhanced by increasing the core 130 rotation rate, utilizing rounded wire (or increasing the size (or number) of the core groove(s) 440), optimizing the wind angle of the coils, or various other means. Additionally, the integrity of the core 130 is enhanced by use of a duplex spring core in one embodiment.

Figure 4:
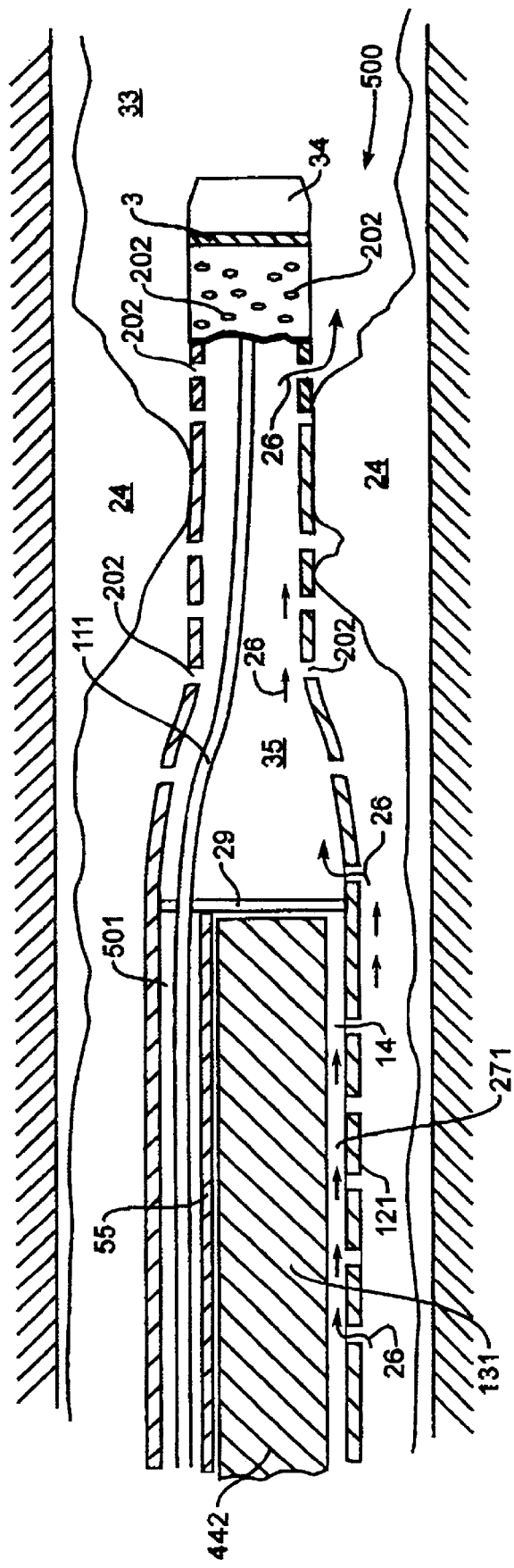
FIG. 4 is a cross-sectional view of another embodiment of a perfusion catheter having a common lumen and placed within a stenosed artery.

Referring to FIG. 4 an alternate perfusion catheter 500 embodiment is shown having a common lumen 35. Again, a core 131 is disposed within a shaft lumen 271. The distal portion of the catheter includes a common lumen 35 capable of accommodating both the core 131 and the guidewire 111. In practice, however, the core 131 and the guidewire 111 are not disposed within the common lumen 35 simultaneously. Rather, a core barrier 55 is provided separating a guidewire lumen 501 from the shaft lumen 271.

The guidewire lumen 501 originates at a proximal portion of the perfusion catheter 500 and proceeds forward merging into the common lumen 35, which itself terminates in a distal tip 34. The guidewire 111 is retracted from the distal tip 34 and common lumen 35 into the guidewire lumen 501 as the core 131 enters the common lumen 35.

The common lumen perfusion catheter 500 is equipped with radio-opaque markers in the form of a bifurcation marker 29 and a distal tip marker 3. The markers 29, 3 are formed of a radiologically dense material which can be detected with fluoroscopy. These markers 29, 3 define the common lumen 35. That is, the bifurcation marker 29, is disposed circumferentially within the shaft 121 at a point lined up with the distal end of the core barrier 55 (or the proximal end of the common lumen 35). Whereas the distal tip marker 3 is disposed circumferentially within the shaft 121 at the distal tip 34 (or the distal end of the common lumen 35).

While the configuration of the common lumen catheter 500 embodiment of FIG. 4 is different from the catheter 300, 400 of FIGS. 2 and 3, a plurality of ports 202 and a core groove 442 are nevertheless similar. The plurality of ports 202 allows fluid communication between the shaft lumen 271 and the arterial passage 33 such that a flow of blood 26 may enter the shaft lumen 271 proximal to any stenosed arterial segment 24. The flow of blood 26 is allowed to continue within the shaft lumen 271 until it exits the plurality of ports 202 distal to the stenosed arterial segment 24. Meanwhile, a core groove 442 acts to draw in, propel, and eventually expel fluid (plasma or otherwise) and air with respect to the shaft lumen 271.

Embodiments of the invention include a catheter adapted to avoid ischemic episodes when the catheter is placed within stenosed or constricted segments of an artery. Additionally, embodiments of the invention include catheters particularly beneficial as IVUS catheters, but may also be beneficial for other purposed or catheter types. Embodiments of the invention allow catheterization teams to image such locations in a manner that reduced the severity or occurrences of ischemia and saves procedure time. Embodiments of the invention allow and even promote the flow of blood past a stenotic area while the artery is being imaged during IVUS and other catheter procedures. Although exemplary embodiments of the invention have been shown and described in the form of particular IVUS perfusion catheters, many changes, modifications, and substitutions may be made without departing from the spirit and scope of this invention. For example, the present invention would be applicable to any catheter or catheter procedure traversing a stenosis or narrowed body lumen in which a rotating core may be accommodated within a shaft lumen.

I claim:

1. A perfusion catheter comprising:
   a longitudinally extending shaft having a shaft lumen there through;
   a plurality of ports extending through said longitudinally extending shaft;
   a rotatable core disposed within said shaft lumen, said rotatable core including a spring; and
   a core groove about said rotatable core, said core groove being between turns of said spring.

2. The perfusion catheter of claim 1 wherein said core groove is spiraled about said core.

3. The perfusion catheter of claim 1 wherein said core groove originates proximal of a proximal-most portion of said plurality of ports when said core occupies a distal-most position within said shaft lumen.

4. The perfusion catheter of claim 1 wherein said plurality of ports extend through said longitudinally extending shaft at a distal portion thereof, said rotatable core upon rotation to pump a fluid through said distal portion via said plurality of ports.

5. The perfusion catheter of claim 1 wherein said longitudinally extending shaft is of a structural integrity to protect vasculature from said core when said longitudinally extending shaft is inserted thereinto and said core is rotated.

6. The perfusion catheter of claim 1 wherein said longitudinally extending shaft is resistant to entanglement with said core as said core is rotated.

7. The perfusion catheter of claim 1 further including a device disposed on said core, said longitudinally extending shaft being resistant to entanglement with said device as said core and said device are rotated.

8. The perfusion catheter of claim 1 wherein said shaft comprises a permeable screen material providing said plurality of ports.

9. The perfusion catheter of claim 1 wherein said spring surrounds an inner spring to comprise a duplex spring.

10. The perfusion catheter of claim 9 wherein said spring and said inner spring are oppositely wound.

11. The perfusion catheter of claim 1 further comprising a monorail tip with a guidewire lumen there through.

12. The perfusion catheter of claim 1 wherein said core has a core length shorter than a shaft length of said longitudinally extending shaft.

13. The perfusion catheter of claim 12 further comprising:
    a core proximal portion;
    a shaft proximal portion; and
    a stopping mechanism, to prevent said core proximal portion from moving distal of said shaft proximal portion.

14. The perfusion catheter of claim 13 wherein said core has a distal-most position created by said stopping mechanism, said core terminating at a point up to about 4.0 mm proximal a distal-most portion of said longitudinally extending shaft when said core is at said distal-most position.

15. The perfusion catheter of claim 1 further comprising a floppy tip disposed at a distal portion of said core.

16. A perfusion catheter comprising:
    a longitudinally extending shaft having a shaft lumen there through;
    a plurality of ports extending through said longitudinally extending shaft;
    a rotatable core disposed within said shaft lumen;
    a core groove about said rotatable core;
    a floppy tip disposed at a distal portion of said rotatable core; and
    a floppy tip coil disposed within said floppy tip.

17. A method of maintaining circulation across a narrowed vessel wall during catheterization thereat, said method comprising:
    guiding a shaft of a catheter across said narrowed vessel wall, said shaft having a plurality of ports there through at a distal portion of said shaft and a retractable core disposed within a lumen of said shaft; and
    retracting said core proximally in order to expose said plurality of ports to allow a flow of blood into a shaft lumen of said shaft,
    wherein said core has a shorter length than said shaft lumen and said core includes a floppy tip disposed at a distal portion of said core, such that said core does not completely block said plurality of ports when said core is advanced into said shaft lumen, and
    wherein said floppy tip comprises a coil disposed within said floppy tip and terminates in a ball.

18. A method as in claim 17 further comprising:
    rotating said core.

19. A method as in claim 17 wherein said core comprises a stopping mechanism to prevent slippage of entire said core into said shaft lumen.

20. A method of maintaining circulation across narrowed vessel portion during catheterization thereat, said method comprising:
    guiding a shaft of a catheter across said narrowed vessel portion, said shaft having a plurality of ports there through; and
    rotating a core within said shaft, said core having a core groove for advancing fluids within a lumen of said shafts,
    wherein said core has a shorter length than said shaft lumen and said core includes a floppy tip disposed at a distal portion of said core, such that said core does not completely block said plurality of ports when said core is advanced into said shaft lumen, and
    wherein said floppy tip comprises a coil disposed within said floppy tip and terminates in a ball.

21. The method of claim 20 further comprising:
    spraying a flush within a lumen of said catheter shaft after said guiding; and
    propelling said flush toward a distal-most portion of said catheter shaft.

22. The method of claim 21 wherein said rotating provides said propelling.

23. The method of claim 20 further comprising drawing a flow of blood into a shaft lumen of said shaft across said plurality of ports at a point proximal to said narrowed vessel portion after said guiding.

24. The method of claim 23 wherein said rotating provides said drawing.

25. The method of claim 23 further comprising retracting said core to a point proximal of said narrowed vessel portion after said guiding to enhance said drawing.

26. The method of claim 20 further comprising advancing a flow of blood within a shaft lumen of said shaft distally past said narrowed vessel portion after said guiding.

27. The method of claim 26 wherein said rotating provides said advancing.

28. The method of claim 20 further comprising forcing a flow of blood out of a shaft lumen of said shaft at a point distal said narrowed vessel portion after said guiding.

29. The method of claim 28 wherein said rotating provides said forcing.

30. The method of claim 20 further comprising agitating air bubbles within a shaft lumen of said shaft to mix with blood within said shaft lumen.

31. The method of claim 30 wherein said rotating provides said agitating.

32. A perfusion catheter comprising:
- a longitudinally extending shaft having a shaft lumen there through;
- a plurality of ports extending through said longitudinally extending shaft; and
- a core disposed within said shaft lumen, said core being at least one of rotatable and retractable,
- wherein said core has a shorter length than said shaft lumen and said core includes a floppy tip disposed at a distal portion of said core, such that said core does not completely block said plurality of ports when said core is advanced into said shaft lumen, and
- wherein said floppy tip comprises a floppy tip coil disposed within said floppy tip.

33. The perfusion catheter of claim 32 wherein said core is rotatable and also retractable.

34. The perfusion catheter of claim 33 wherein said core, when retracted, exposes at least a portion of said plurality of ports.

35. The perfusion catheter of claim 32 wherein said plurality of ports extend through said longitudinally extending shaft at a distal portion thereof, said core upon rotation to pump a fluid through said distal portion via said plurality of ports.

36. The perfusion catheter of claim 32 wherein said longitudinally extending shaft is of a structural integrity to protect vasculature from said core when said longitudinally extending shaft is inserted thereinto and said core is rotated.

37. The perfusion catheter of claim 32 wherein said longitudinally extending shaft is resistant to entanglement with said core as said core is rotated.

38. The perfusion catheter of claim 32 further including a device disposed on said core, said longitudinally extending shaft being resistant to entanglement with said device as said core and said device are rotated.

39. The perfusion catheter of claim 32 wherein said shaft comprises a permeable screen material providing said plurality of ports.

40. The perfusion catheter of claim 32 further comprising a tip with a guidewire lumen there through.

41. The perfusion catheter of claim 32 further comprising:
- a core proximal portion;
- a shaft proximal portion; and
- a stopping mechanism, to prevent said core proximal portion from moving distal of said shaft proximal portion.

42. The perfusion catheter of claim 41 wherein said core has a distal-most position created by said stopping mechanism, said core terminating at a point up to about 4.0 mm proximal a distal-most portion of said longitudinally extending shaft when said core is at said distal-most position.

43. The perfusion catheter of claim 32 wherein said floppy tip terminates in a ball.

* * * * *